(12) United States Patent
Yong et al.

(10) Patent No.: US 12,024,489 B2
(45) Date of Patent: Jul. 2, 2024

(54) COMPLEX SALT OF RUPESTONIC ACID AND ALKALOID, PREPARATION METHOD THEREFOR AND USE THEREOF

(71) Applicant: XIAMEN INSTITUTE OF RARE EARTH MATERIALS, Fujian (CN)

(72) Inventors: Jianping Yong, Fujian (CN); Canzhong Lu, Fujian (CN)

(73) Assignee: XIAMEN INSTITUTE OF RARE EARTH MATERIALS, Fujian (CN)

( * ) Notice: Subject to any disclaimer, the term of this patent is extended or adjusted under 35 U.S.C. 154(b) by 0 days.

(21) Appl. No.: 17/805,006

(22) Filed: Jun. 1, 2022

(65) Prior Publication Data
US 2023/0219875 A1 Jul. 13, 2023

(30) Foreign Application Priority Data
Jan. 12, 2022 (CN) .......................... 202210032992.0

(51) Int. Cl.
C07C 59/82 (2006.01)
A61K 31/4375 (2006.01)
A61K 45/06 (2006.01)

(52) U.S. Cl.
CPC .......... C07C 59/82 (2013.01); A61K 31/4375 (2013.01); A61K 45/06 (2013.01)

(58) Field of Classification Search
CPC ... C07C 59/82; C07C 2602/30; C07D 471/22; C07B 2200/07; A61K 31/4375; A61K 45/06; A61K 31/19; A61K 31/205; A61K 47/55; A61P 35/00
See application file for complete search history.

(56) References Cited

U.S. PATENT DOCUMENTS

2010/0087523 A1* 4/2010 Aisa ........................ A61P 31/12
564/189

OTHER PUBLICATIONS

Obul, M., Wang, X., Zhao, J. et al. Structural modification on rupestonic acid leads to highly potent inhibitors against influenza virus. Mol Divers 23, 1-9 (2019) (Year: 2019).*
Pu et al. Matrine induces apoptosis via targeting CCR7 and enhances the effect of anticancer drugs in non-small cell lung cancer in vitro. Innate Immun. 2018;24(7):394-399. (Year: 2018).*
(Continued)

*Primary Examiner* — Matthew P Coughlin
*Assistant Examiner* — Ashli Ariana Chicks
(74) *Attorney, Agent, or Firm* — NKL Law; Allen Xue (57) ABSTRACT

A complex salt formed from a compound of formula (I) and an alkaloid, a preparation method therefor and use thereof are provided. In particular, a complex salt formed from rupestonic acid and matrine, oxymatrine, sophocarpine and sophoridine, or a composition thereof, has potential efficacy in treating a tumor/cancer or preparing related medicaments.

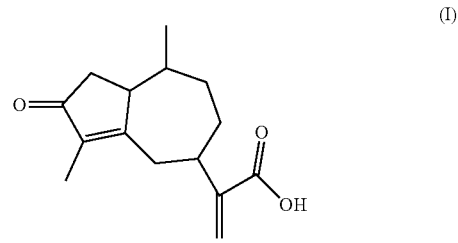

14 Claims, 9 Drawing Sheets (56) References Cited

OTHER PUBLICATIONS

Wang et al. *Sophora alopecuroides* L.: an ethnopharmacological, phytochemical, and pharmacological review J. Ethnopharmacol., 248 (2020), Article 112172. (Year: 2020).*

Luo et al. Cell, 2009, 136, pp. 823-837. (Year: 2009).*

Cancer Vaccines: The Types, How They Work, and Which Cancers They Treat, obtained from https://www.mskcc.org/cancer-care/diagnosis-treatment/cancer-treatments/immunotherapy/cancer-vaccines on Sep. 6, 2023. (Year: 2023).*

Can Lung Cancer Be Prevented?, obtained from https://www.cancer.org/cancer/types/lung-cancer/causes-risks-prevention/prevention.html on Sep. 6, 2023. (Year: 2023).*

Can I Lower My Risk of Breast Cancer?, obtained from https://www.cancer.org/cancer/types/breast-cancer/risk-and-prevention/can-i-lower-my-risk.html on Sep. 6, 2023. (Year: 2023).*

Can Stomach Cancer Be Prevented?, obtained from https://www.cancer.org/cancer/types/stomach-cancer/causes-risks-prevention/prevention.html on Sep. 6, 2023. (Year: 2023).*

* cited by examiner

COMPLEX SALT OF RUPESTONIC ACID AND ALKALOID, PREPARATION METHOD THEREFOR AND USE THEREOF

TECHNICAL FIELD

The present disclosure relates to the technical field of pharmaceuticals, and in particular to a complex salt of rupestonic acid and alkaloid, a preparation method therefor and use thereof in treating tumors/cancers.

BACKGROUND

Cancer has become the leading fatal disease worldwide. Cancer may occur in various organs and tissues at any age. The main cancers leading to death include lung cancer, stomach cancer, liver cancer, colon cancer, breast cancer and the like. Some small-molecule anti-cancer drugs have been used clinically, and some compound anti-cancer drugs are under pre-clinical study. However, most cancer patients are not aware of the disease until it is in the middle to late stage, and the overall effect of clinical treatment is poor. In particular, the treatment of cancer is beset with difficulties due to the continuous occurrence of multi-drug resistance. Therefore, it is extremely urgent to develop novel anti-cancer drugs with high activity and low side effects to meet clinical needs. Having relatively mild toxic and side effects, the traditional Chinese medicines have a long history of being administered in China. The discovery of new drug candidates or lead drugs from the traditional Chinese medicines is the mainstream of drug development nowadays.

Matrine, oxymatrine, sophocarpine and sophoridine are alkaloids obtained from dried roots, plants and fruits of *Sophora flavescens* Ait of Leguminosae, which have a wide range of pharmacological activities (Zhang Mingfa, Shen Yaqin, Advances in research on anti-sarcoma effects of matrine-type alkaloids, *Drug Evaluation Research*, 2018, 41(11): 2117-2122). The matrine injection is clinically used for treating chronic viral hepatitis B, and leukopenia resulted from radiotherapy and chemotherapy for tumors and other causes.

*Artemisia Rupestris* L. is mainly distributed in Xinjiang, Central Asia, Europe and other places, and has a long history of being used in folk medicine in Xinjiang. It is clinically used for treating diseases such as dyspepsia, abdominal distention and pain, hepatitis, snake bite, common cold and fever. The compound formulation "Compound of *Artemisia rupestris* granule" with *Artemisia Rupestris* L. as the main component under NMPA approval number Z200226711 is clinically used for expelling wind by diaphoresis and treating diseases such as viral cold and swollen sore throat. Rupestonic acid is one of the characteristic compounds in *Artemisia Rupestris* L., and is a sesquiterpene compound containing multiple functional groups, and the rupestonic acid and the derivatives thereof have stronger activity against influenza virus and herpes virus [(1) Derivates of Rupestonic Acid and Uses Thereof, ZL200710180021.6; (2) Advances in Studies on the Rupestonic Acid Derivatives as Anti-influenza Agents. *Mini-Reviews in Medical Chemistry*. 2013, 13(2): 310-315].

The present disclosure provides a complex salt prepared from rupestonic acid and alkaloid, such as matrine, oxymatrine, sophocarpine and sophoridine. The results show that the complex salt has anti-tumor activity and can be used for treating a tumor/cancer disease.

SUMMARY

The present disclosure provides a complex salt formed from a compound of formula (I) and an alkaloid:

wherein the alkaloid may be selected from matrine, oxymatrine, sophocarpine and sophoridine. According to an embodiment of the present disclosure, the compound of formula (I) and the alkaloid may be in a molar ratio of 1:(0.5-5), such as 1:(0.8-2), illustratively 1:1.

According to an embodiment of the present disclosure, the compound of formula (I) has a structure as shown in formula (II):

According to an embodiment of the present disclosure, the complex salt may be selected from a complex salt of rupestonic acid and matrine, a complex salt of rupestonic acid and oxymatrine, a complex salt of rupestonic acid and sophocarpine, and a complex salt of rupestonic acid and sophoridine, specifically having a structure shown as follows:

Complex salt of rupestonic acid and matrine

Complex salt of rupestonic acid and oxymatrine

Complex salt of rupestonic acid and sophocarpine

Complex salt of rupestonic acid and sophoridine

The present disclosure also provides a preparation method for the above complex salt, which comprises dissolving the compound of formula (I) and alkaloid in an organic solvent, and mixing the solution to obtain the complex salt.

According to an embodiment of the present disclosure, the compound of formula (I) and the alkaloid may be in a molar ratio of 1:(0.5-5), such as 1:(0.8-2), illustratively 1:1.

According to an embodiment of the present disclosure, the organic solvent is selected from single solvents or mixed solvents that are capable of dissolving both of the compounds, such as methanol, ethanol, chloroform, acetone, toluene, dichloromethane and ethyl acetate, and preferably is methanol or acetone.

The present disclosure also provides a pharmaceutical composition comprising a therapeutically effective amount of the complex salt or the composition thereof.

According to an embodiment of the present disclosure, the pharmaceutical composition further comprises one or more pharmaceutically acceptable auxiliary materials.

According to an embodiment of the present disclosure, the pharmaceutical composition may also further comprise one or more additional therapeutic agents.

The present disclosure provides use of the complex salt or the composition thereof in treating tumors/cancers.

According to an embodiment of the present disclosure, the cancer may be lung cancer, breast cancer, gastric cancer or cervical cancer.

The present disclosure provides use of the complex salt or the composition thereof in preparing a medicament for treating a tumor/cancer.

The present disclosure also provides a method for treating a tumor/cancer, which comprises administering a prophylactically or therapeutically effective amount of the complex salt compound of formula (I) to a patient.

In some embodiments, the patient is a human.

When used as a medicament, the complex salt of the present disclosure may be administered in the form of a pharmaceutical composition. The pharmaceutical composition may be prepared in any pharmaceutically acceptable formulation form, such as a solid oral formulation, an injection formulation, an emulsion, a cream, a tincture and an ointment, and the injection formulation may be a small needle injection and a lyophilized injection. Those compositions may be prepared in a manner well known in the pharmaceutical arts and may be administered by a variety of routes depending on whether local or systemic treatment is desired and the area to be treated. The pharmaceutical composition can be administered topically (e.g., by transdermal, dermal, ocular and mucosal routes, including intranasal, vaginal and rectal delivery routes), pulmonarily (e.g., by inhalation or insufflation of powders or aerosols, including by nebulizer; by intratracheal and intranasal routes), orally or parenterally. The parenteral administration includes intravenous, intra-arterial, subcutaneous, intraperitoneal or intramuscular injection or infusion; or intracranial (e.g., intrathecal or intracerebroventricular) administration. The pharmaceutical composition may be administered parenterally in a single bolus form, or may be administered by, for example, continuous infusion pump. The pharmaceutical composition and formulation administered topically may include a transdermal patch, an ointment, a lotion, a cream, a gel, a drop, a suppository, a spray, a liquid and a powder. Conventional pharmaceutical carriers, water, powders or oily bases, thickeners and the like may be necessary or desirable.

In preparing the composition of the present disclosure, the active ingredient is typically mixed with an excipient, diluted by the excipient or contained in such a carrier, for example, in the form of a capsule, a sachet, paper or other containers. When used as a diluent, the excipient may be a solid, semi-solid or liquid material that serves as a vehicle, a carrier or a medium for the active ingredient. Thus, the composition may be in the form of a tablet, a granule, a sustained release formulation, a pill, a powder, a lozenge, a sachet, a cachet, an elixir, a suspension, an emulsion, a solution, a syrup, an aerosol (solid or dissolved in a liquid vehicle); an ointment, soft and hard gelatin capsules, a suppository, a sterile injectable solution and a sterile packaged powder containing, for example, up to 10% by weight of the active compound.

Certain examples of suitable excipients include lactose, glucose, sucrose, sorbitol, mannitol, starch, acacia, calcium phosphate, alginate, tragacanth, gelatin, calcium silicate, microcrystalline cellulose, polyvinylpyrrolidone, cellulose, water, syrup and methylcellulose. The formulation may further contain a lubricant such as talc, magnesium stearate and mineral oil; a wetting agent; an emulsifier and a suspending agent; a preservative such as methyl benzoate and hydroxypropyl benzoate; a sweetening agent and a flavoring agent. The composition of the present disclosure may be formulated by the methods known in the art so as to provide immediate, sustained or delayed release of the active ingredient after administration to the patient.

The composition may be formulated in unit dosage forms containing about 5-1000 mg, typically about 100-500 mg, of the active ingredient per dose. The term "unit dosage form" refers to physically discrete single dosage units suitable for use in human patients and other mammals, each unit containing a predetermined amount of active substance mixed with a suitable pharmaceutical excipient that can produce the desired therapeutic effect by calculation.

The active compound may be effective in a wide range of doses and is generally administered in a pharmaceutically effective amount. However, it will be understood that the amount of the compound actually administered is usually determined by a physician, in the light of the relevant circumstances, including the disorder to be treated, the selected route of administration, the compound actually administered; the age, weight and response of an individual patient; the severity of patient's symptoms, etc.

For the preparation of solid compositions such as tablets, the main active ingredient is mixed with pharmaceutical excipients to form solid preformulation compositions containing a homogeneous mixture of the compounds of the present disclosure. When those preformulation compositions are referred to be homogeneous, it is meant that the active ingredient is generally distributed evenly throughout the composition so that the composition may be readily divided into equally effective unit dosage forms such as tablets, pills and capsules. The solid preformulation is then divided into unit dosage forms of the above type containing, for example, about 0.1-1000 mg of the active ingredient of the present disclosure.

The tablets or pills of the present disclosure may be coated or compounded to obtain a dosage form affording the advantage of long-acting effect. For example, the tablets or pills contain an inner dosage component and an outer dosage component, the latter being in the form of an envelope of the former. The two components may be separated by an enteric coating layer which serves to prevent the disintegration in the stomach to allow the inner component to pass through the duodenum entirely or to be delayed in release. A variety of substances may be used for such enteric coating layers or coatings, including various polymeric acids and mixtures of polymeric acids and such substances as shellac, cetyl alcohol and cellulose acetate.

Liquid forms in which the compound and composition of the present disclosure may be incorporated for oral or injection administration include aqueous solutions, suitably flavored syrups, aqueous or oil suspensions; emulsions flavored with edible oils such as cottonseed oil, sesame oil, coconut oil or peanut oil; and elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described above. In certain embodiments, the composition is administered by the oral or intranasal or respiratory route for local or systemic effect. The composition may be nebulized by using inert gases. The nebulized solution may be inhaled directly from the nebulizing device or the nebulizing device may be attached to a face mask, tent or an intermittent positive pressure ventilator. The solution, suspension or powder compositions may be administered orally, or nasally by means of a device which delivers the formulation in a suitable manner.

The amount of the compound or composition administered to a patient varies depending on the drug administered, the purpose of the administration such as for prophylaxis or therapy; the condition of the patient, the mode of administration, etc. In therapeutic applications, the composition may be administered to a patient suffering from a disease in an amount sufficient to cure or at least partially arrest the symptoms of the disease and its complications. The effective dosage should be determined based on the state of the disease being treated and the judgment of the attending clinician, which depends on factors such as the severity of the disease, and the age, weight and general condition of the patient.

The composition administered to the patient may be in the form of the pharmaceutical composition as described above. These compositions may be sterilized by conventional sterilization techniques or by filter sterilization. The aqueous solutions may be packaged for use as is, or lyophilized, and the lyophilized formulation is mixed with a sterile aqueous carrier prior to administration. The compound formulation usually has a pH of 3-11, more preferably 5-9, and most preferably 7-8. It will be understood that the use of certain excipients, carriers or stabilizers as described above may result in the formation of a pharmaceutical salt.

The therapeutic dosage of the compound of the present disclosure may depends, for example, on the particular use of the treatment, the manner in which the compound is administered, the health and condition of the patient, and the judgment of the prescribing physician. The proportion or concentration of the compound of the present disclosure in the pharmaceutical composition may vary depending on a variety of factors including the dosage, chemical properties (e.g., hydrophobicity), and the route of administration. For example, the compound of the present disclosure may be provided for parenteral administration by a physiologically buffered aqueous solution containing about 0.1-10% w/v of the compound. Certain typical dosage ranges from about 1 µg/kg body weight/day to about 1 g/kg body weight/day. In certain embodiments, the dosage ranges from about 0.01 mg/kg body weight/day to about 100 mg/kg body weight/day. The dosage is likely to depend on such variables as the type and degree of progression of the disease or disorder, the general health condition of the particular patient, the relative biological potency of the compound selected, the excipient formulation and its route of administration. Effective doses can be extrapolated from dose-response curves derived from in vitro or animal model test systems.

According to an embodiment of the present disclosure, the auxiliary material comprises one of or a mixture of more of a filler, an adhesive, a disintegrant, a lubricant, a flavoring agent, an enteric coating and a sustained-release material.

According to an embodiment of the present disclosure, the filler comprises one of or a mixture of more of lactose, sucrose, dextrin, starch, mannitol, sorbitol, dicalcium phosphate, calcium carbonate and microcrystalline cellulose.

According to an embodiment of the present disclosure, the adhesive comprises one of or a mixture of more of sucrose, starch, sodium carboxymethylcellulose, methyl cellulose, polyethylene glycol and water.

According to an embodiment of the present disclosure, the disintegrant comprises one of or a mixture of more of starch, crospovidone, croscarmellose sodium, low-substituted hydroxypropylcellulose and sodium carboxymethylcellulose.

According to an embodiment of the present disclosure, the lubricant comprises one of or a mixture of more of talc, magnesium stearate, stearic acid, colloidal silicon dioxide, polyethylene glycol-4000 and polyethylene glycol-6000.

According to an embodiment of the present disclosure, the flavoring agent comprises one of or a mixture of more of sucrose, sorbitol, saccharin sodium, maltitol, stevioside and aspartame.

According to an embodiment of the present disclosure, the sustained-release material comprises one of or a mixture of more of hydroxypropyl methylcellulose and guar gum with different specifications of viscosity.

Beneficial Effects

The present disclosure provides a complex salt compound of formula (I), a preparation method therefor and use thereof, which is found to have an anti-tumor effect by testing the complex salts of rupestonic acid and matrine, oxymatrine, sophocarpine and sophoridine. The complex salt compound or the composition thereof has potential efficacy in treating tumor/cancer diseases.

DETAILED DESCRIPTION

Figure 1:
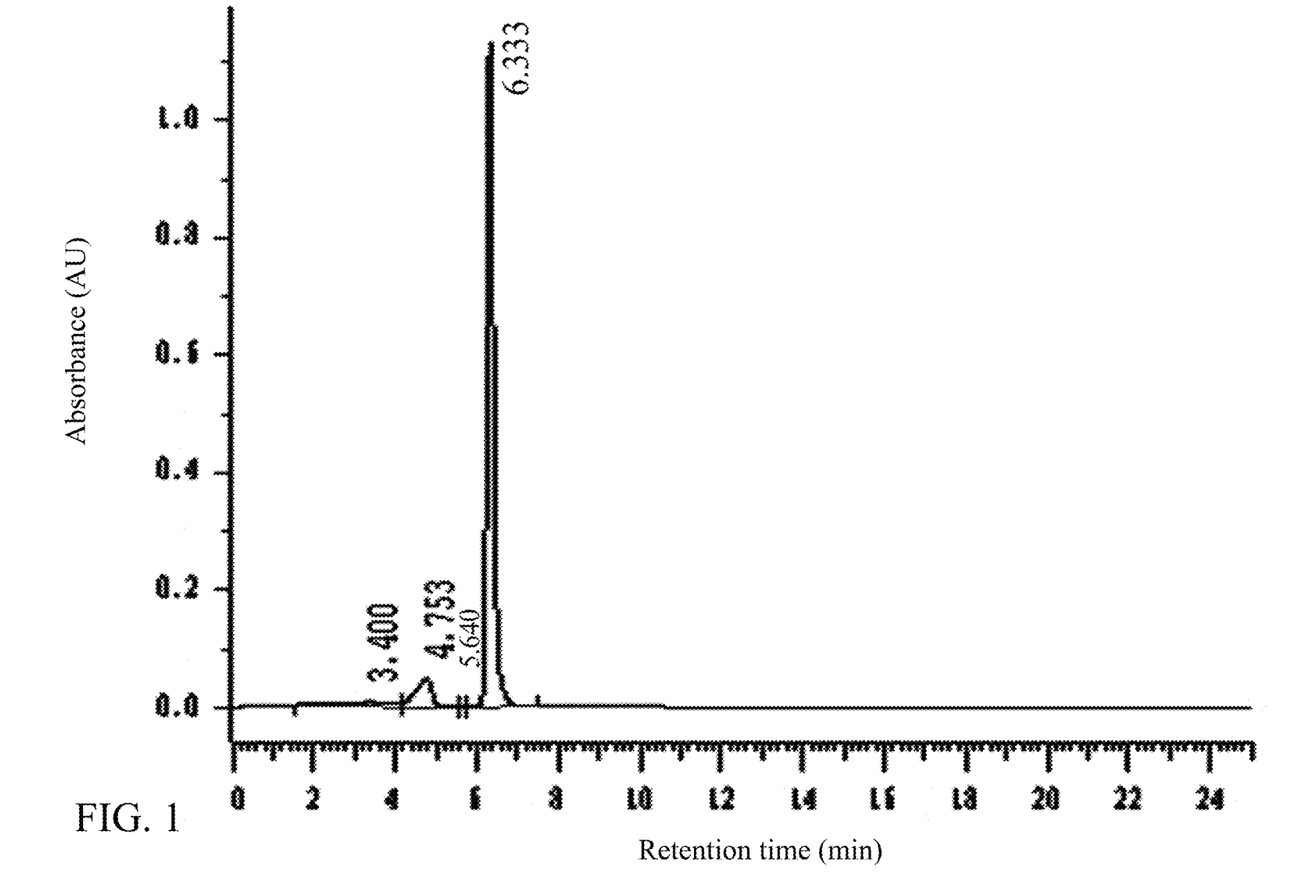
FIG. 1: An HPLC chromatogram of matrine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 2:
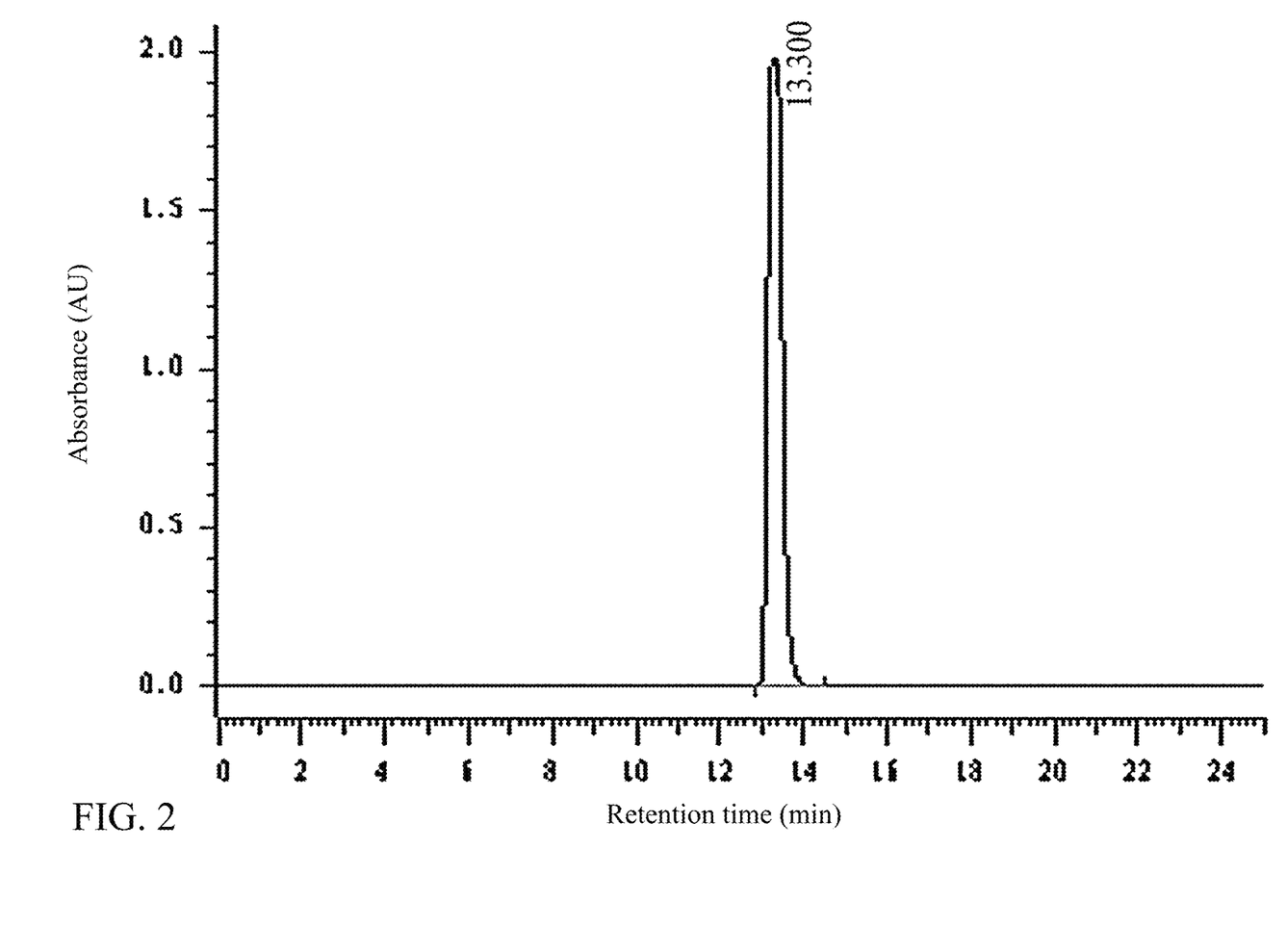
FIG. 2: An HPLC chromatogram of rupestonic acid, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 3:
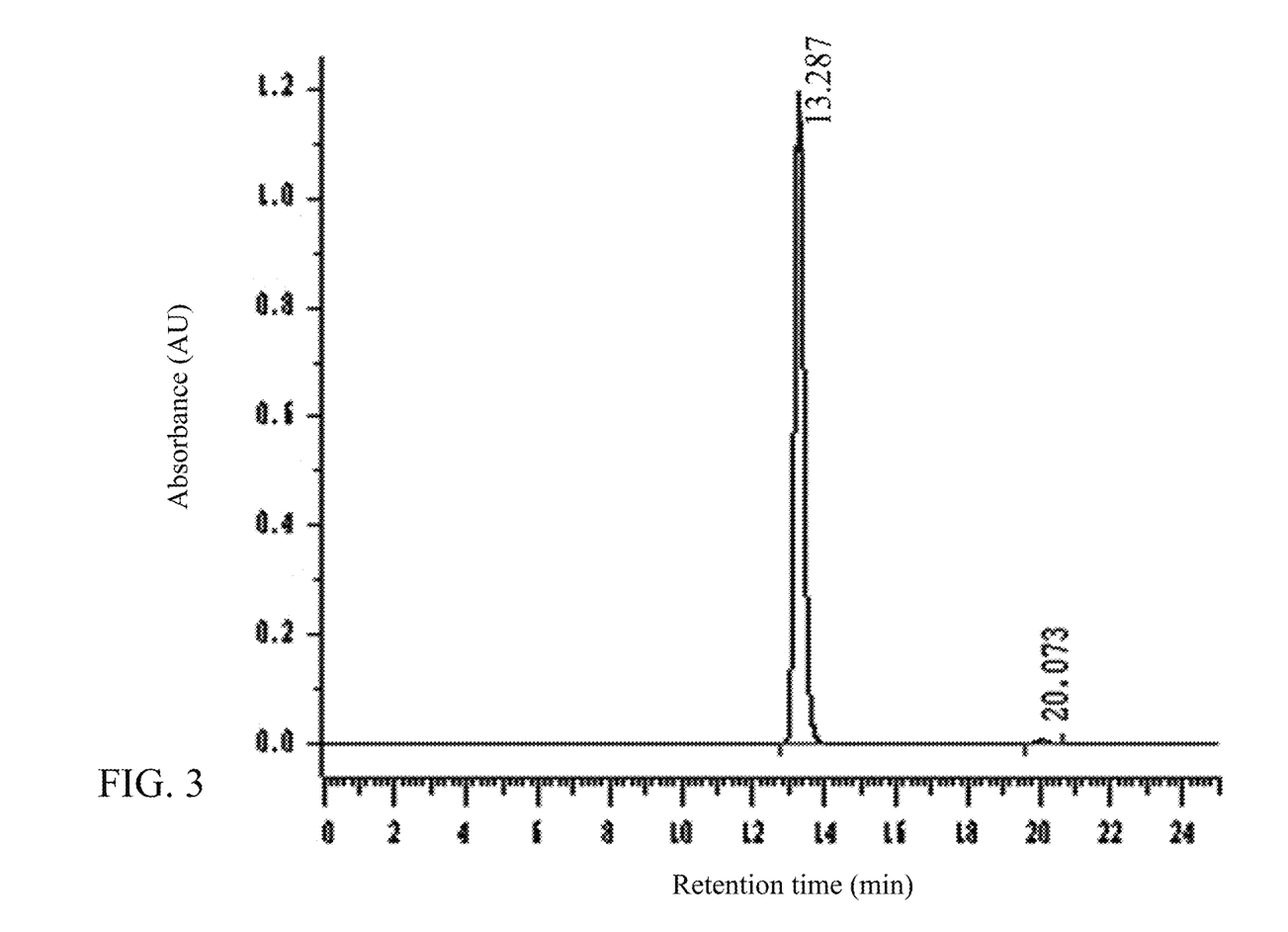
FIG. 3: An HPLC chromatogram of a complex salt of rupestonic acid and matrine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 4:
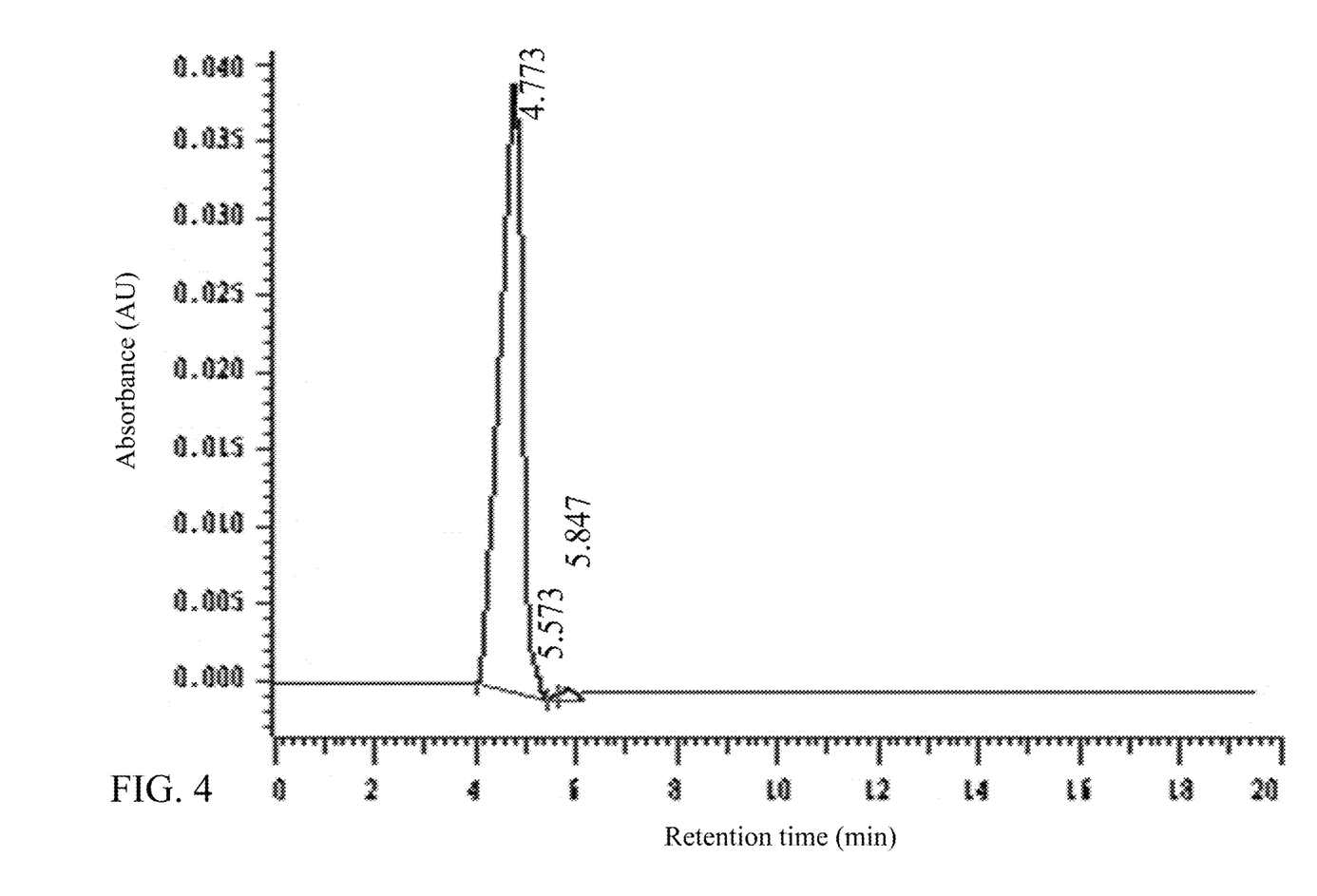
FIG. 4: An HPLC chromatogram of oxymatrine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 5:
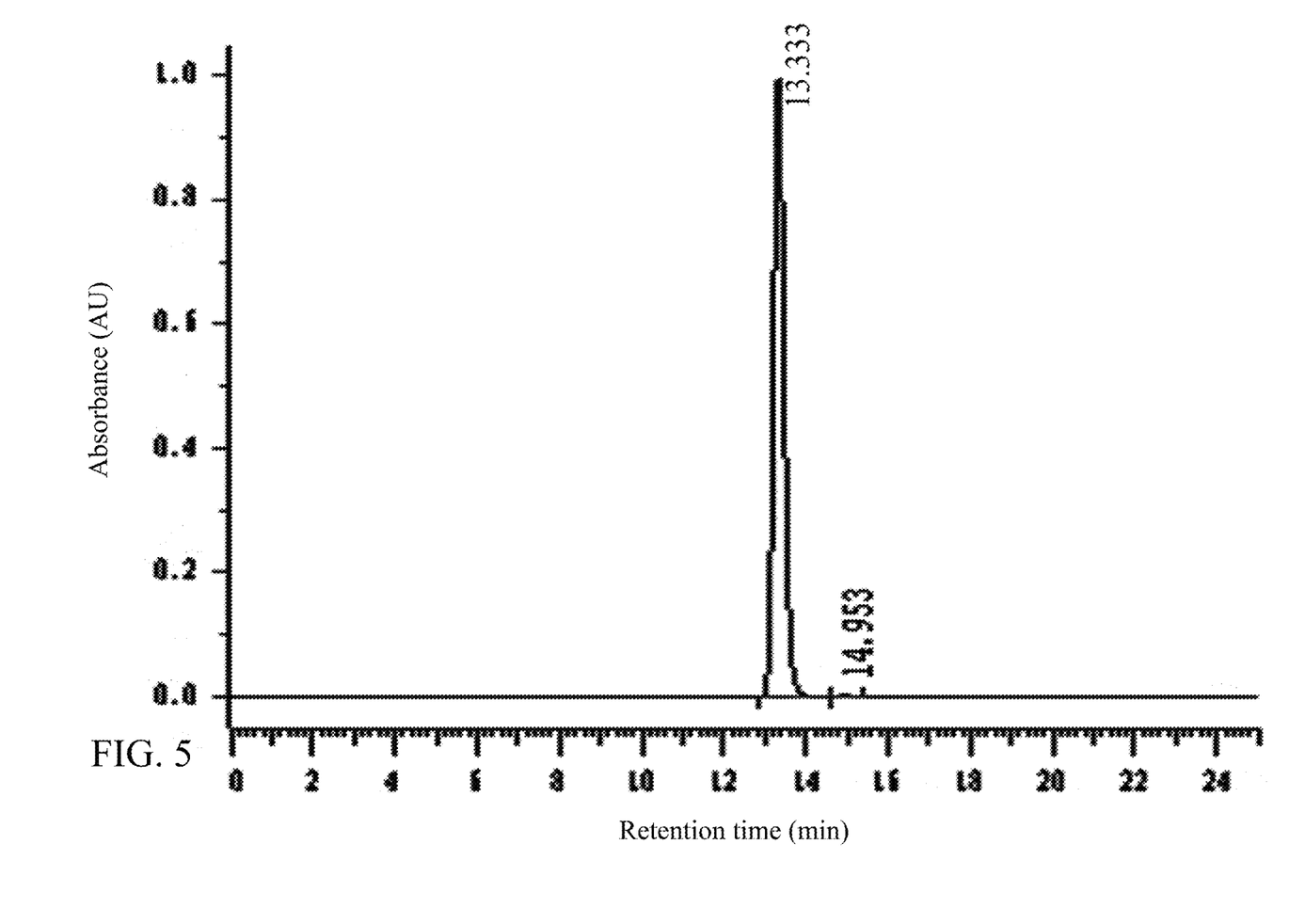
FIG. 5: An HPLC chromatogram of a complex salt of rupestonic acid and oxymatrine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 6:
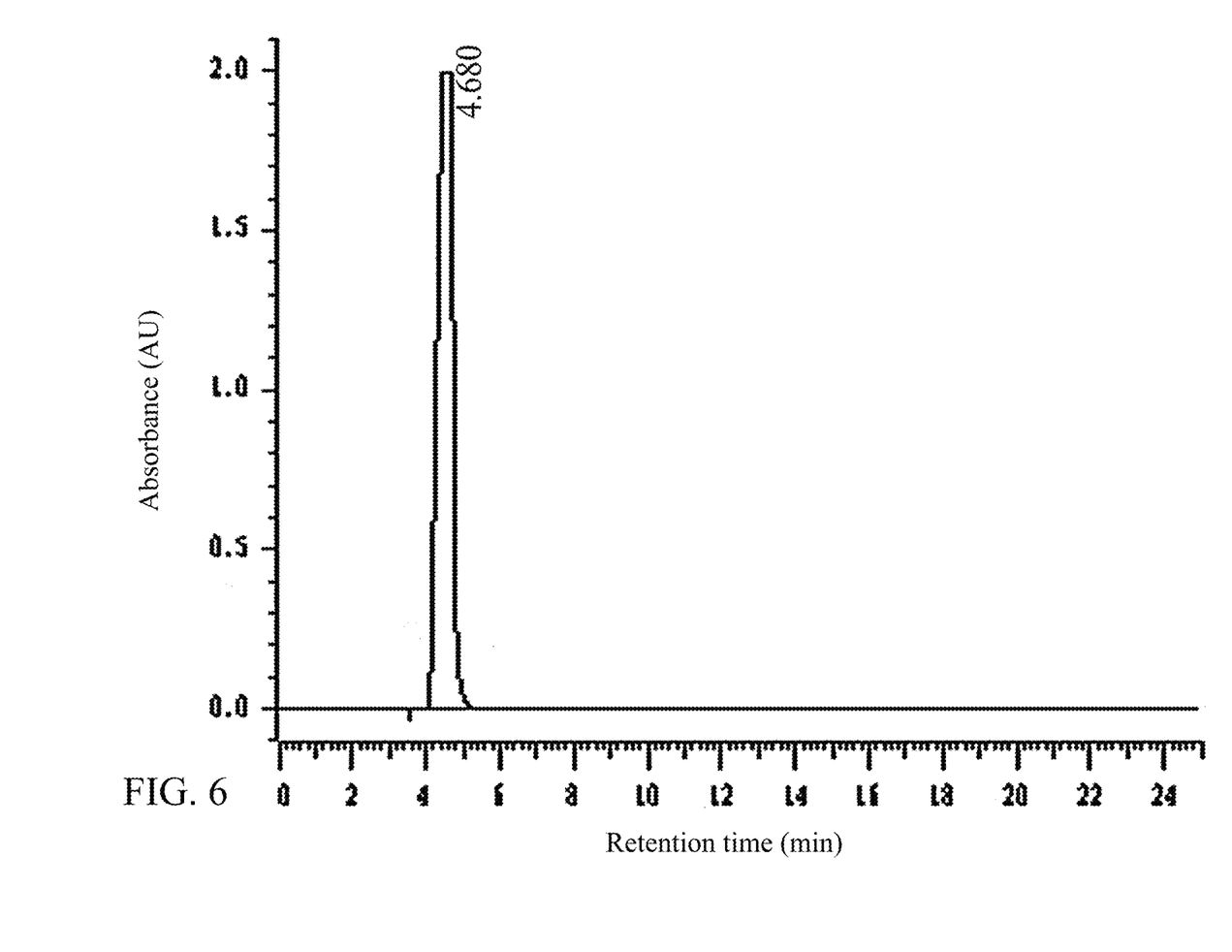
FIG. 6: An HPLC chromatogram of sophocarpine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 7:
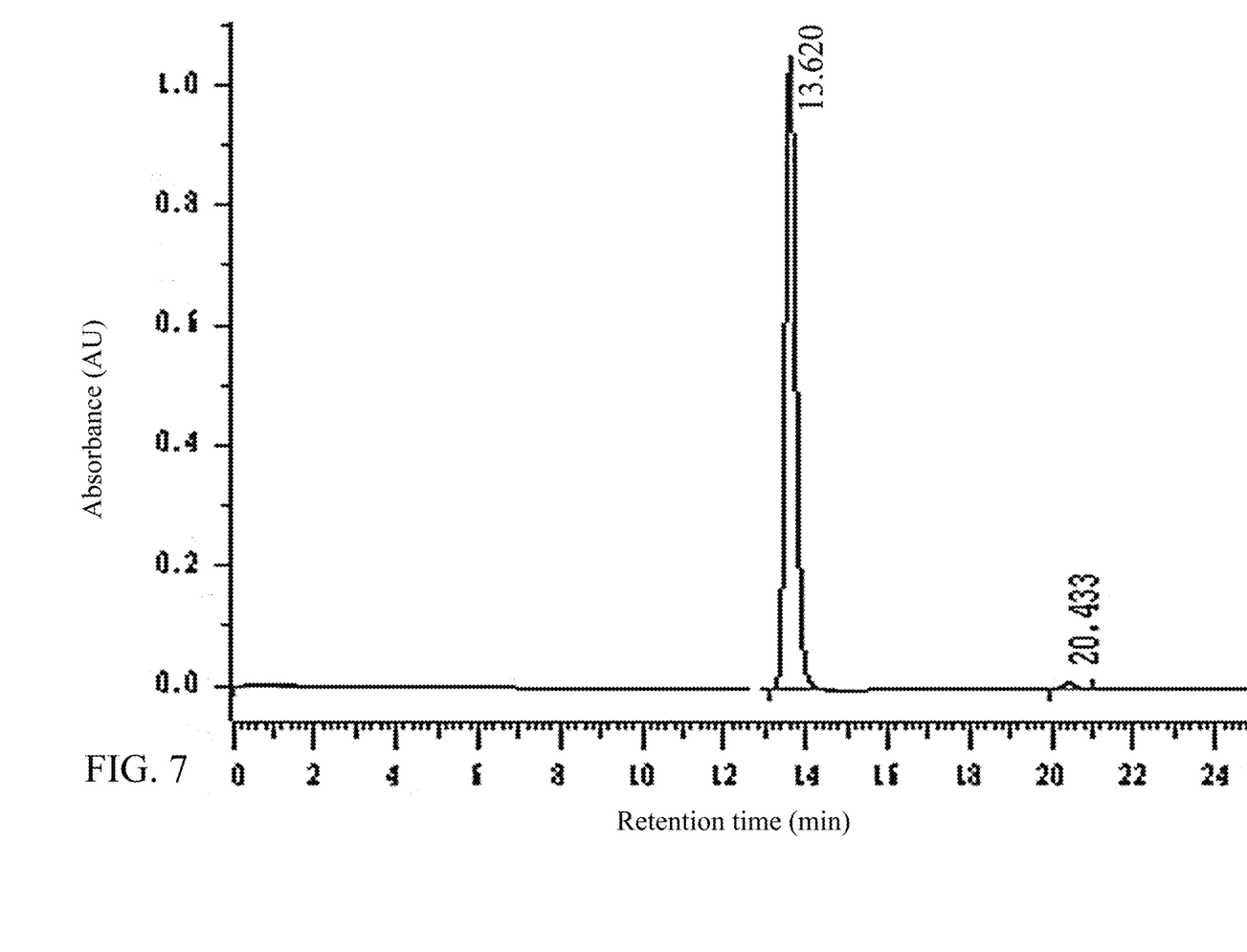
FIG. 7: An HPLC chromatogram of a complex salt of rupestonic acid and sophocarpine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 8:
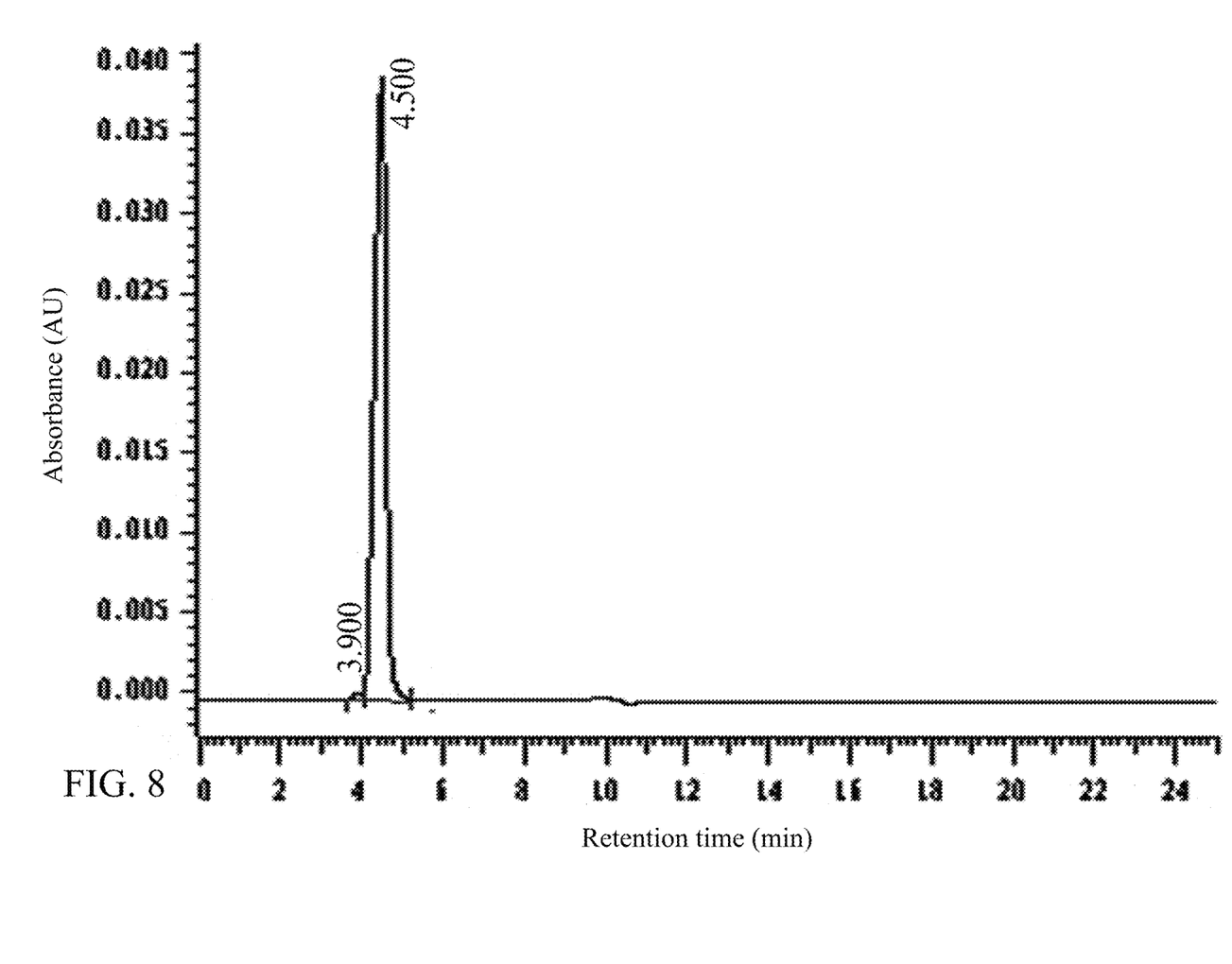
FIG. 8: An HPLC chromatogram of sophoridine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.
Figure 9:
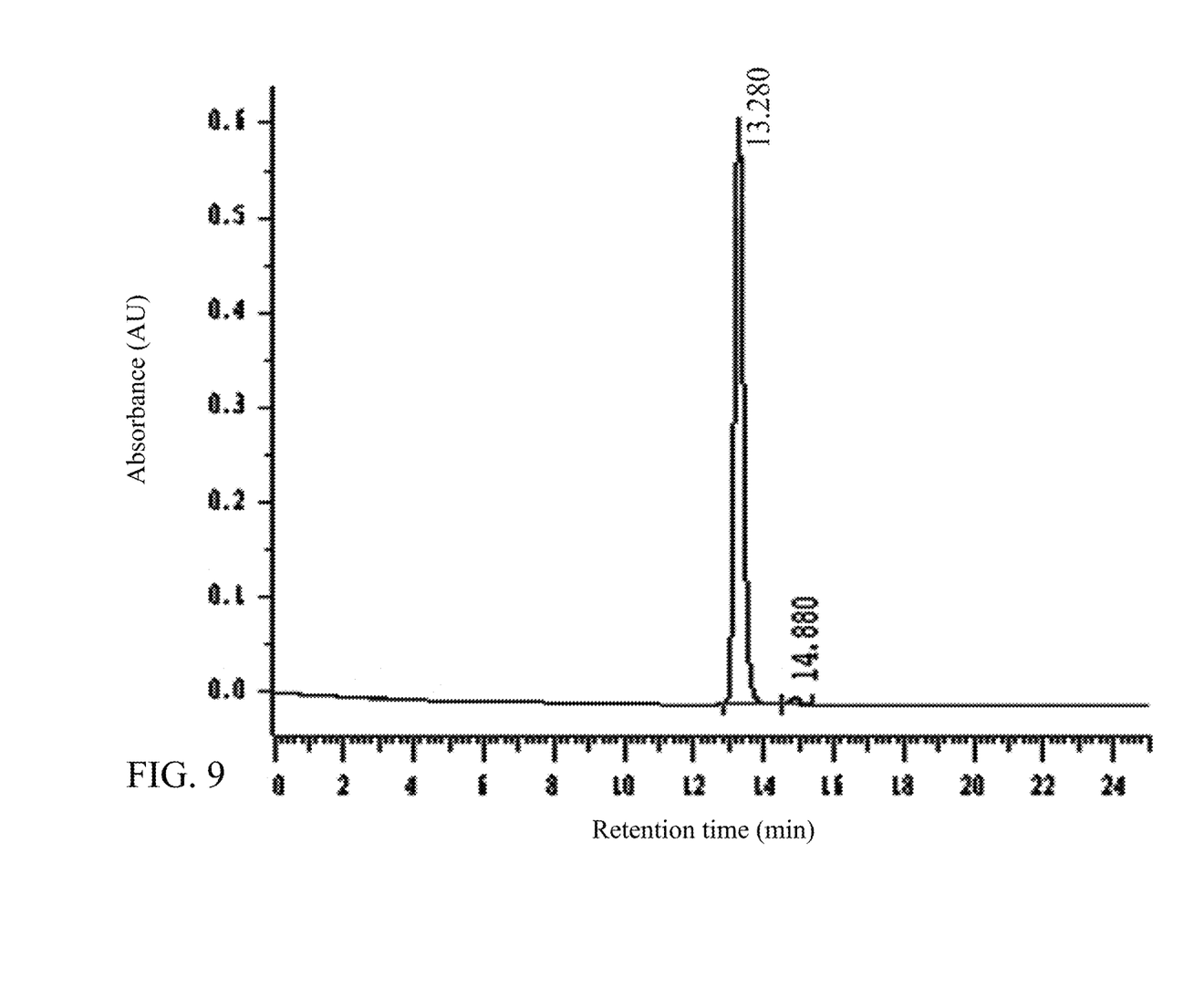
FIG. 9: An HPLC chromatogram of a complex salt of rupestonic acid and sophoridine, with chromatographic conditions as follows: $C_{18}$ column; mobile phase:$V_{methanol}$:$V_{water\ (containing\ 0.3\%\ phosphoric\ acid)}$, 7:3; detection wavelength: 254 nm.

The technical scheme of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the above content of the present disclosure are encompassed within the protection scope of the present disclosure.

Unless otherwise stated, the starting materials and reagents used in the following examples are all commercially available products or can be prepared by known methods.

Instruments and Reagents:

Rupestonic acid (98%, provided by professor Haji Akber Aisa, Xinjiang Technical Institute of Physics and Chemistry, Chinese Academy of Sciences); matrine, oxymatrine, sophocarpine and sophoridine (purity>98%, all purchased from Shanxi Yuning Biotechnology Co., Ltd.); LC3000N high performance liquid chromatograph (Beijing Chuangxintongheng Chromatography Technology Co., Ltd.); Hitachi L2000 high performance liquid chromatograph (Hitachi); CCK8 (Shanghai Beibo Biotechnology Co., Ltd.); DMEM high glucose medium (Thermo Fisher Scientific (Suzhou) Instruments Co., Ltd.); EDTA (pancreatin) (gibco); Foetal Bovine Serum (Biological Industries); phosphate buffered saline; 96-well cell culture plate; multifunctional microplate reader.

Example 1. Preparation of a Complex Salt of Rupestonic Acid and Matrine 0.124 g (0.5 mmol) of rupestonic acid and 0.124 g (0.5 mmol) of matrine were added into a 20 mL round-bottom flask, followed by the addition of 5 mL of dried methanol, and the mixture was stirred at room temperature for 30 min. After the reaction was completed as detected by HPLC, the solution was concentrated under reduced pressure to obtain the complex salt of rupestonic acid and matrine (crude product). The crude product was purified by preparative HPLC to obtain a colorless sticky oil (chromatographic conditions: $C_{18}$ column; mobile phase: $V_{methanol}$:$V_{water\ (containing\ 0.3\%\ phosphoric\ acid)}$, 7:3; detection wavelength: 254 nm), HPLC purity: 98.9%.

Example 2. Preparation of a Complex Salt of Rupestonic Acid and Oxymatrine

-continued 0.124 g (0.5 mmol) of rupestonic acid and 0.132 g (0.5 mmol) of oxymatrine were added into a 20 mL round-bottom flask, followed by the addition of 5 mL of dried methanol, and the mixture was stirred at room temperature for 30 min. After the reaction was completed as detected by HPLC, the solution was concentrated under reduced pressure to obtain the complex salt of rupestonic acid and matrine (crude product). The crude product was purified by preparative HPLC to obtain a colorless sticky oil (chromatographic conditions: $C_{18}$ column; mobile phase: $V_{methanol}$:$V_{water\ (containing\ 0.3\%\ phosphoric\ acid)}$, 7:3; detection wavelength: 254 nm), HPLC purity: 97.3%.

Example 3. Preparation of a Complex Salt of Rupestonic Acid and Sophocarpine 0.124 g (0.5 mmol) of rupestonic acid and 0.123 g (0.5 mmol) of sophocarpine were added into a 20 mL round-bottom flask, followed by the addition of 5 mL of dried methanol, and the mixture was stirred at room temperature for 30 min. After the reaction was completed as detected by HPLC, the solution was concentrated under reduced pressure to obtain the complex salt of rupestonic acid and sophocarpine (crude product). The crude product was purified by preparative HPLC to obtain a colorless sticky oil (chromatographic conditions: $C_{18}$ column; mobile phase: $V_{methanol}$:$V_{water\ (containing\ 0.3\%\ phosphoric\ acid)}$, 7:3; detection wavelength: 254 nm), HPLC purity: 95.3%.

Example 4. Preparation of a Complex Salt of Rupestonic Acid and Sophoridine 0.124 g (0.5 mmol) of rupestonic acid and 0.123 g (0.5 mmol) of sophoridine were added into a 20 mL round-bottom flask, followed by the addition of 5 mL of dried methanol, and the mixture was stirred at room temperature for 30 min. After the reaction was completed as detected by HPLC, the solution was concentrated under reduced pressure to obtain the complex salt of rupestonic acid and sophoridine (crude product). The crude product was purified by preparative HPLC to obtain a colorless sticky oil (chromatographic conditions: $C_{18}$ column; mobile phase: $V_{methanol}$:$V_{water\ (containing\ 0.3\%\ phosphoric\ acid)}$, 7:3; detection wavelength: 254 nm), HPLC purity: 98.1%.

Example 5. In Vitro Anti-Tumor Activity Test

The obtained *Artemisia Rupestris* complex salts were subjected to an in vitro anti-tumor activity test, in which the in vitro inhibitory activity of the *Artemisia Rupestris* complex salts on the lung adenocarcinoma cell line (A549) and cervical carcinoma cell line (Hela) was mainly researched. The specific test process was illustrated by the process for testing the lung adenocarcinoma cell line (A549):

1. Preparation of Test Sample

The prepared *Artemisia Rupestris* complex salt was weighed, added into a 5 mL plastic centrifuge tube and diluted to 1 mL with DMSO, to obtain a test sample at an initial concentration. Then the test sample at an initial concentration was serially diluted with DMSO to obtain test samples in 5 different concentration gradients in sequence, which were stored in a refrigerator at 4° C. for later use.

2. Incubation and Inhibitory Activity Test of the Lung Adenocarcinoma Cell Line (A549)

The lung adenocarcinoma cell line (A549) was incubated in an incubator for 24 h under the conditions of 37° C., 5% $CO_2$, and saturated humidity. When the cells were in logarithmic growth phase, the culture supernatant was discarded, and the residue was digested with 0.25% trypsin-EDTA solution. Then, the digestion was terminated with high glucose medium. The cells were seeded in a 96-well plate with a cell density of 5000 cells/well. The 96-well plate was incubated in an incubator for 24 h. Then the cell culture supernatant in the 96-well plate was discarded. 100 μL of high glucose medium was added to the 96-well plate, and test samples at different concentrations were added to wells at 1 μL/well (5 duplicate wells were set for each concentration). After the plate was incubated in an incubator for 48 h under the conditions of 37° C., saturated humidity and 5% $CO_2$, 10 μL of CCK8 was added to each well, and the plate was then incubated in the incubator at 37° C. for 1-4 h. The absorbance of each well at 450 nm was measured on a multifunctional microplate reader. Inhibition rate %= [($OD_{control\ cells}$−$OD_{treatment\ cells}$)/($OD_{control\ cells}$−$OD_{blank}$)]× 100. Negative control was a mixed solution of $V_{high\ glucose\ medium}$ and $V_{DMSO}$ at a ratio of 10:1.

The process for testing the inhibition of those compounds on the cervical cancer cell line (Hela) was the same as above. The results of the inhibition on the two tumor cell lines are shown in Table 1.

TABLE 1

Test results of the activity of the compounds on two tumor cell lines

| Compound | IC$_{50}$ (μM) | |
| --- | --- | --- |
| | A549 | Hela |
| Rupestonic acid | Inactive | Inactive |
| Matrine | 6.37 × 10$^3$ | 774.0 |
| Oxymatrine | 7.32 × 10$^5$ | 0.95 |
| Sophocarpine | 240.9 | 121.7 |
| Sophoridine | 1.6 × 10$^4$ | 1.49 × 10$^3$ |
| Complex salt of rupestonic acid and matrine | 1.492 | 11.78 |
| Complex salt of rupestonic acid and oxymatrine | / | 25.17 |
| Complex salt of rupestonic acid and sophocarpine | 713.7 | 114.8 |
| Complex salt of rupestonic acid and sophoridine | 61.26 | 17.90 |

Examples of the present disclosure have been described above. However, the present disclosure is not limited to the above examples. Any modification, equivalent, improvement and the like made without departing from the spirit and principle of the present disclosure shall fall within the protection scope of the present disclosure.

The invention claimed is:

1. A complex salt formed from a compound of formula (I) and an alkaloid:

(I)

wherein the alkaloid is selected from matrine, oxymatrine, and sophoridine.

2. The complex salt according to claim 1, wherein the compound of formula (I) has a structure as shown in formula (II):

(II)

3. The complex salt according to claim 1, wherein the complex salt is selected from a complex salt of rupestonic acid and matrine, a complex salt of rupestonic acid and oxymatrine, a complex salt of rupestonic acid and sophocarpine, and a complex salt of rupestonic acid and sophoridine.

4. The complex salt according to claim 1, wherein a molar ratio between the compound of formula (I) and the alkaloid is 1:(0.5-5).

5. A preparation method for the complex salt according to claim 1, comprising mixing the compound of formula (I) and the alkaloid in an organic solvent to obtain the complex salt.

6. The preparation method for the complex salt according to claim 5, wherein the organic solvent is a single solvent or a mixed solvent capable of dissolving the compound of formula (I) and the alkaloid.

7. A pharmaceutical composition comprising a therapeutically effective amount of the complex salt according to claim 1.

8. The pharmaceutical composition according to claim 7, further comprising one or more pharmaceutically acceptable auxiliary materials.

9. A method for treating a cancer, comprising administering an effective amount of the complex salt according to claim 1 to a subject in need thereof, wherein the cancer is a non-small-cell lung cancer or cervical cancer.

10. The complex salt according to claim 4, wherein the molar ratio between the compound of formula (I) and the alkaloid is 1:(0.8-2).

11. The preparation method for the complex salt according to claim 5, wherein a molar ratio between the compound of formula (I) and the alkaloid is 1:(0.5-5).

12. The preparation method for the complex salt according to claim 6, wherein the molar ratio between the compound of formula (I) and the alkaloid is 1:(0.8-2).

13. The preparation method for the complex salt according to claim 6, wherein the organic solvent is selected from methanol, ethanol, chloroform, acetone, toluene, dichloromethane, ethyl acetate, and mixtures thereof.

14. The pharmaceutical composition according to claim 8, further comprising one or more therapeutic agents.

* * * * *